United States Patent
Perler et al.

(10) Patent No.: US 11,123,106 B2
(45) Date of Patent: Sep. 21, 2021

(54) BONE SEGMENT ATTACHMENT SYSTEM AND METHOD

(71) Applicant: InMotus Medical LLC, Carmel, IN (US)

(72) Inventors: Adam D. Perler, St. Petersburg, FL (US); James A. Zoellner, Avon, IN (US); James Q. Spitler, Ocoee, FL (US)

(73) Assignee: InMotus Medical LLC, Carmel, IN (US)

( * ) Notice: Subject to any disclaimer, the term of this patent is extended or adjusted under 35 U.S.C. 154(b) by 190 days.

(21) Appl. No.: 16/419,537

(22) Filed: May 22, 2019

(65) Prior Publication Data

US 2019/0357941 A1    Nov. 28, 2019

Related U.S. Application Data

(60) Provisional application No. 62/675,150, filed on May 22, 2018.

(51) Int. Cl.
*A61B 17/86* (2006.01)
*A61B 17/68* (2006.01)
*A61B 17/80* (2006.01)

(52) U.S. Cl.
CPC ........ *A61B 17/683* (2013.01); *A61B 17/8004* (2013.01); *A61B 17/86* (2013.01); *A61B 17/8052* (2013.01)

(58) Field of Classification Search
CPC ... A61B 17/86; A61B 17/8685; A61B 17/683; A61F 2/4225
See application file for complete search history.

(56) References Cited

U.S. PATENT DOCUMENTS

| 4,011,603 A | 3/1977 | Steffee |
| 5,133,761 A | 7/1992 | Krouskop |

(Continued)

FOREIGN PATENT DOCUMENTS

WO    2016/115172    7/2016

OTHER PUBLICATIONS

International Search Report and Written Opinion dated Sep. 5, 2019 for corresponding International Application No. PCT/US2019/033614.

*Primary Examiner* — Olivia C Chang
(74) *Attorney, Agent, or Firm* — David Meibos; Maywood IP Law

(57) ABSTRACT

A system for attaching first and second bone segments together may include a first component and a second component. The first component may have a first component bone engagement end implantable into a first bore formed in the first bone segment, and a first component attachment end. The second component may have a second component bone engagement end implantable into a second bore formed in the second bone segment, and a second component attachment end with a first projection that is movable, in response to a temperature change of the first projection, between insertion and locking configurations. In the insertion configuration, the first projection may be positioned to avoid interference with withdrawal of the second component attachment end from the first component attachment end. In the locking configuration, the first projection may be positioned to interfere with withdrawal of the second component attachment end from the first component attachment end.

15 Claims, 8 Drawing Sheets

(56) References Cited

U.S. PATENT DOCUMENTS

| | | |
|---|---|---|
| 6,413,260 B1 | 7/2002 | Berrevoets et al. |
| 6,454,808 B1 | 9/2002 | Masada |
| 9,072,562 B2 | 7/2015 | Weiner et al. |
| 2014/0018812 A1 | 1/2014 | Graham |
| 2017/0290614 A1 | 10/2017 | Weiner et al. |
| 2018/0303615 A1 | 10/2018 | Papaloizos |

BONE SEGMENT ATTACHMENT SYSTEM AND METHOD

RELATED APPLICATIONS

This application claims the benefit of U.S. Provisional Patent Application Ser. No. 62/675,150, filed on May 22, 2018, entitled BONE SEGMENT ATTACHMENT SYSTEM AND METHOD. The foregoing is incorporated by reference as though set forth herein in its entirety.

TECHNICAL FIELD

The present disclosure relates to surgical systems, and methods. More specifically, the present disclosure relates to improved surgical implants for securing a first bone segment, such as a proximal phalanx, to a second bone segment, such as a middle phalanx.

BACKGROUND

There are many instances in which two bone segments of the body are to be secured together. For example, fragments of a broken bone may be secured through the use of surgical implants. Alternatively, joints between bones may be effectively immobilized to alleviate pain or correct deformities by securing the bone segments on either side of the joint together.

Current technologies for attaching bone segments together may be insufficient to meet the needs of patients. Some known systems include male and female components that can only be secured together in a limited number of relative axial positions. A first relative axial position may not sufficiently place the two bone segments in contact with each other to allow them to fuse while an adjacent axial position may not be attainable due to interference of the bone segments with each other. Thus, in some situations, the resolution with which the male and female components are attachable to each other may be insufficient to provide the desired bone in-growth between the two bone segments.

Furthermore, some known bone segment attachment systems may not provide sufficiently secure fixation to prevent the bone segments from moving relative to each other, after implantation of the bone segment attachment system. Such motion may inhibit proper bone fusion and/or healing.

SUMMARY

The various systems and methods of the present disclosure have been developed in response to the present state of the art, and in particular, in response to the problems and needs in the art that have not yet been fully solved by currently available surgical instruments, systems, and methods for repairing an odontoid fracture in a patient.

According to one embodiment, a system for attaching a proximal phalanx to a middle phalanx may include a female component and a male component. The female component may include a female component bone engagement end implantable into a first bore formed in one of the proximal phalanx and the middle phalanx, and a receiving end. The female component bone engagement end may have one or more female component bone engagement features configured to engage the first bore to retain the female component bone engagement end within the first bore. The receiving end may have a receiving end bore defining a bore axis. The receiving end bore may be accessible through an opening, and may include a first bore portion having a first bore wall, with a first diameter, and a second bore portion having a second bore wall positioned such that the first bore wall is between the second bore wall and the opening, the second bore wall having a second diameter larger than the first diameter. The male component may include a male component bone engagement end implantable into a second bore formed in the other of the proximal phalanx and the middle phalanx, and a protruding end. The male component bone engagement end may have one or more male component bone engagement features configured to engage the second bore to retain the male component bone engagement end within the second bore. The protruding end may have a protrusion defining a protrusion axis. The protrusion may have a first projection that is movable, in response to a temperature change of the first projection, between an insertion configuration in which the first projection does not extend radially beyond the first diameter, and a locking configuration in which the first projection extends radially beyond the first diameter such that the first projection is positioned to interfere with withdrawal of the protrusion from the receiving end bore.

The receiving end bore may further have a shoulder extending generally radially between the first bore wall and the second bore wall. The first projection, in the locking configuration, may press against the shoulder.

The first projection may have a rod that, with the first projection positioned within the second bore portion of the receiving end bore, is bent toward the second bore wall.

In the insertion configuration, the rod may be bent at an obtuse angle. In the locking configuration, the rod may be bent at an acute angle.

The protrusion may further have a second projection positioned on an opposite side of the protrusion axis from the first projection. The second projection may also be movable, in response to the temperature change, between the insertion configuration and the locking configuration.

The first projection may be formed at least partially of Nitinol.

The temperature change may include the first projection to cause the first projection to move from the insertion configuration to the locking configuration.

The temperature change may include heating the first projection to cause the first projection to move from the insertion configuration to the locking configuration.

The male component bone engagement end may define a bone engagement axis nonparallel to the protrusion axis.

According to one embodiment, a method for attaching a first bone segment and a second bone segment together may include positioning a first component proximate the first bone segment. The first component may include a first component bone engagement end, and a first component attachment end. The method may further include implanting the first component bone engagement end into a first bore formed in the first bone segment, and positioning a second component proximate the second bone segment. The second component may include a second component bone engagement end, and a second component attachment end with a first projection. The method may further include implanting the second component bone engagement end into a second bore formed in the second bone segment, assembling the second component attachment end together with the first component attachment end with the first projection in an insertion configuration, and applying a temperature change to the first projection to move the first projection from an insertion configuration to a locking configuration. With the second component attachment end assembled together with the first component attachment end, in the insertion configuration, the first projection may be positioned such that the first projection does not interfere with withdrawal of the second component attachment end from the first component attachment end. Further, with the second component attachment end assembled together with the first component attachment end, in the locking configuration, the first projection may be positioned to interfere with withdrawal of the second component attachment end from the first component attachment end.

The first bone segment may be one of a proximal phalanx and a middle phalanx. The second bone segment may be the other of the proximal phalanx and the middle phalanx. The method may further include forming the first bore in one of a proximal phalanx and a middle phalanx, and forming the second bore in the other of the proximal phalanx and the middle phalanx.

The first component attachment end may have an attachment end bore. The second component attachment end may have a protrusion. Assembling the second component attachment end together with the first component attachment end may include inserting the protrusion into the attachment end bore. The protrusion may include the first projection.

The attachment end bore may be accessible through an opening in the first component attachment end. The attachment end bore may have a first bore portion having a first bore wall, with a first diameter, a second bore portion having a second bore wall positioned such that the first bore wall is between the second bore wall and the opening, the second bore wall having a second diameter larger than the first diameter, and a shoulder extending generally radially between the first bore wall and the second bore wall. Assembling the second component attachment end together with the first component attachment end may include positioning the first projection within the second bore portion. In the insertion configuration, the first projection may not extend radially beyond the first diameter. Moving the first projection from the insertion configuration to the locking configuration may include causing the first projection to extend radially beyond the first diameter such that the first projection is positioned to interfere with withdrawal of the protrusion from the attachment end bore.

The first projection may be a rod that, with the first projection positioned within the second bore portion of the attachment end bore, is bent toward the second bore wall. In the insertion configuration, the rod may be bent at an obtuse angle. Moving the first projection from the insertion configuration to the locking configuration may include causing the rod to bend at an acute angle.

According to one embodiment, a system for attaching a first bone segment and a second bone segment together may include a first component and a second component. The first component may have a first component bone engagement end implantable into a first bore formed in the first bone segment, and a first component attachment end. The second component may have a second component bone engagement end implantable into a second bore formed in the second bone segment, and a second component attachment end with a first projection that is movable, in response to a temperature change of the first projection, between an insertion configuration and a locking configuration. In the insertion configuration, with the second component attachment end assembled together with the first component attachment end, the first projection may be positioned such that the first projection does not interfere with withdrawal of the second component attachment end from the first component attachment end. In the locking configuration, with the second component attachment end assembled together with the first component attachment end, the first projection may be positioned to interfere with withdrawal of the second component attachment end from the first component attachment end.

The first bone segment may be one of a proximal phalanx and a middle phalanx. The second bone segment may be the other of the proximal phalanx and the middle phalanx.

The first component attachment end may have an attachment end bore. The second component attachment end may have a protrusion insertable into the attachment end bore, the protrusion having the first projection.

The attachment end bore may be accessible through an opening in the first component attachment end. The attachment end bore may include a first bore portion having a first bore wall, with a first diameter, and a second bore portion having a second bore wall positioned such that the first bore wall is between the second bore wall and the opening, the second bore wall having a second diameter larger than the first diameter, and a shoulder extending generally radially between the first bore wall and the second bore wall. With the second component attachment end assembled together with the first component attachment end, the first projection may be within the second bore portion. In the insertion configuration, the first projection may not extend radially beyond the first diameter. In the locking configuration, the first projection may extend radially beyond the first diameter such that the first projection is positioned to interfere with withdrawal of the protrusion from the attachment end bore.

The first projection may be a rod that, with the first projection positioned within the second bore portion of the attachment end bore, is bent toward the second bore wall. In the insertion configuration, the rod may be bent at an obtuse angle. In the locking configuration, the rod may be bent at an acute angle.

The protrusion may define a protrusion axis. The protrusion may further have a second projection positioned on an opposite side of the protrusion axis from the first projection. The second projection may also be movable, in response to the temperature change, between the insertion configuration and the locking configuration.

BRIEF DESCRIPTION OF THE DRAWINGS

Exemplary embodiments of the disclosure will become more fully apparent from the following description and appended claims, taken in conjunction with the accompanying Figures. Understanding that these Figures depict only exemplary embodiments and are, therefore, not to be considered limiting of the scope of the appended claims, the exemplary embodiments of the present disclosure will be described with additional specificity and detail through use of the accompanying Figures:

DETAILED DESCRIPTION

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method, as represented in FIGS. 1 through 8, is not intended to limit the scope of the disclosure, but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated. The terms "first," "second," etc. are used merely for purposes of differentiation, and do not denote any particular order of steps or positional relationship between elements.

The present disclosure discloses bone segment attachment systems and methods. Such bone segment attachment systems and methods may be designed to attach one bone segment to another bone segment. A bone segment at least includes either a full or partial portion of a bone. In one example, bone segments include two phalanges, while in other examples, the bone segments are other bones in body that are to be fused together, such as the bones of a joint that is to be immobilized. In yet other examples, the bone segments may include two segments of a bone that has been broken. Of course, one skilled in the art may recognize other situations where two bone segments may be attached together; this disclosure contemplates all such situations.

Figure 1:
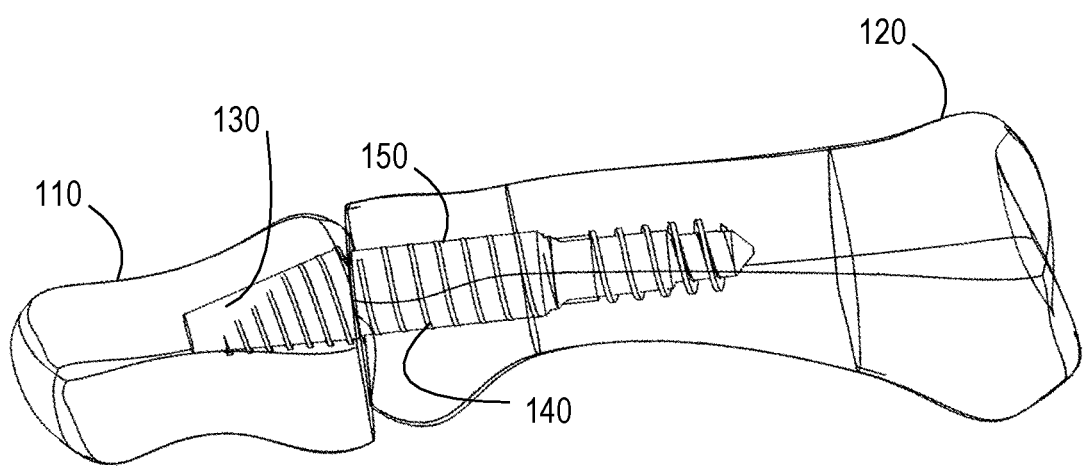
FIG. 1 is a perspective view depicting one exemplary embodiment of a bone segment attachment system.

FIG. 1 is a perspective view depicting one exemplary embodiment of a bone segment attachment system 150. In this embodiment, the bone segment attachment system 150 has been installed to affix a first bone segment 110 and a second bone segment 120. In one example, the bone segment attachment system 150 is installed to ensure contact between a surface of the first bone segment 110 and a surface of the second bone segment 120. Such contact allows the first bone segment 110 to fuse to the second bone segment 120 over a healing period of time.

As mentioned previously, the bone segment attachment system 150 may be used for a wide variety of joints or fractured bones in the body. As shown in FIG. 1, the bone segment attachment system 150 is used for an extremity, namely, the joint between the proximal and middle phalanges. Thus, the first bone segment 110 may be the middle phalanx and the second bone segment 120 may be the proximal phalanx of a human foot. In such a configuration, the bone segment attachment system 150 may be used to treat a condition such as hammertoe, for example, by fusing the joint between the proximal and middle phalanges such that the middle phalanx is secured in a generally rectilinear configuration relative to the middle phalanx.

In one exemplary embodiment, the bone segment attachment system 150 has a male component and a female component wherein each of the male and/or female components include one or more bone engagement features (specifically, male component bone engagement features and female component bone engagement features) configured to engage the corresponding bone segment. In one example, the male component bone engagement features and the female component bone engagement features are each helical threads around an outside surfaces of the components whereby a surgeon implanting the bone segment attachment system 150 may screw the components into corresponding bores in the first bone segment 110 and the second bone segment 120. In another example, the bone engagement features are ridges, barbs, deployable extensions, expandable elements, and/or any other bone engagement features known in the art, for securing an implant to bone in a manner that resists withdrawal of the implant from the bone.

In one exemplary embodiment, a surgeon forms a bore 130 in the first bone segment 110 and forms a bore 140 in the second bone segment 120. The surgeon then inserts the male component partially into the bore 130 of the first bone segment 110 to engage the bone engagement features of the male component with the bore 130. The surgeon also inserts the female component into the bore 140 in the second bone segment 120 to engage the bone engagement features of the female component to the bore 140. Then, the surgeon may secure the female component to the male component as will be further described subsequently. Specific embodiments of the male component and the female component are further described in subsequent figures and paragraphs.

Figure 2:
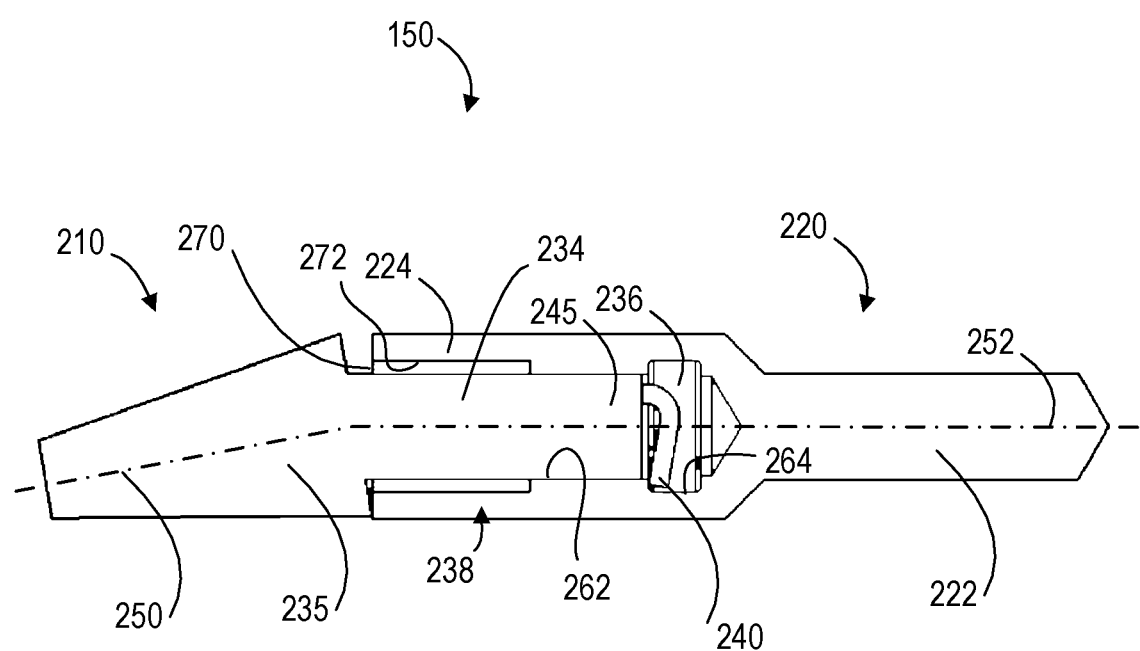
FIG. 2 is a side elevation, section view of the bone segment attachment system of FIG. 1.

FIG. 2 is a side elevation, section view of the bone segment attachment system 150 of FIG. 1. As embodied in FIG. 2, the bone segment attachment system 150 includes a female component 220 and a male component 210. The male component 210 is in the locking configuration.

The female component 220 may be securable in the bore 140 of the second bone segment 120, and may include a receiving end bore 238 for receiving a protrusion 245 on a protruding end 234 of the male component 210. The male component 210 may be securable in the bore 130 of the first bone segment 110.

The male component 210 and the female component 220 may have engagement features that allow the protrusion 245 of male component 210 to be inserted into the female component 220, but restrict withdrawal of the protrusion 245 from the female component 220, as will be described in greater detail subsequently. Thus, in certain embodiments, the male component 210, attached to the first bone segment 110, is pressed into the female component 220 with the female component 220 attached to the second bone segment 120. The male component 210 and the female component 220 are then secured together to allow the first bone segment 110 and the second bone segment 120 to fuse together.

In one embodiment, the female component 220 includes a bone engagement end 222 that includes one or more bone engagement features. In one embodiment, the female component 220 further includes a receiving end 224 that is configured to receive the protruding end 234 of the male component 210. The receiving end 224 includes the receiving end bore 238, which is configured to receive and/or attach to the protruding end 234 of the male component 210 as mentioned previously.

In one example, insertion of the protruding end 234 of the male component 210 into the receiving end bore 238 of the female component 220 causes friction between the protruding end 234 and the receiving end bore 238. However, the mechanism that retains the protruding end 234 in the receiving end bore 238 may not be friction, but rather, mechanical interference between an element on the protruding end 234, and an aspect of the geometry of the receiving end bore 238, as will be set forth in more detail subsequently. Specifically, the protruding end 234 may have one or more projections 240 (hereinafter "projections 240," which includes the option of having only one projection 240).

The projections 240 can selectively protrude, radially, far enough to interfere with withdrawal of the protruding end 234 from the receiving end bore 238. Each of the one or more projections 240 may have an insertion configuration, in which it does not extend far enough to provide such interference, and a locking configuration in which it does extend far enough to interfere with withdrawal of the protruding end 234 from the receiving end bore 238.

In one exemplary embodiment, the receiving end bore 238 comprises a first bore portion 262 and a second bore portion 264. In this embodiment, the first bore portion 262 has a smaller diameter than the second bore portion 264. Thus, as will be further described, the projections 240 of the protruding end 234 may pass through the first bore portion 262 in the insertion configuration with little or no interference. After the projections 240 change to a locking configuration, they may extend radially beyond the radius of the first bore portion 262. The projections 240 may be moved to the locking configuration after passing through the first bore portion 262 and into the second bore portion 264, thus restricting extraction of the protruding end 234 from the receiving end bore 238.

In FIG. 2, the projections 240 generally in the form of bent rods that are bent toward the wall of the receiving end bore 238 when the projections 240 are disposed in the receiving end bore 238. In FIG. 2, the projections 240 are in the locking configuration because they are bent at acute angles in which they extend outward, radially, beyond the radius of the first bore portion 262. Thus, as configured in FIG. 2, the projections 240 mechanically interfere with withdrawal of the protruding end 234 from the receiving end bore 238. In the insertion configuration, which will be shown in FIG. 4, the projections 240 may be more obtusely angled such that the tips of the projections 240 do not extend beyond the radius of the first bore portion 262. If desired, the tips of the projections 240 may be angled such that, in the insertion configuration, they are generally parallel to the interior wall of the receiving end bore 238, and in the locking configuration, they are oriented at greater angles, relative to the interior wall of the receiving end bore 238, so that they extend further radially.

The receiving end bore 238 may be accessible view an opening 270 formed in the receiving end 224. In certain embodiments, the first bore portion 262 may or may not be adjacent to the opening 270. However, in one specific embodiment, and as depicted in FIG. 2, the receiving end bore 238 may have three bore portions: the first bore portion 262, the second bore portion 264, and a third bore portion 272 that is adjacent to the opening 270. The first bore portion 262 may have a diameter similar to that of the protrusion 245 of the protruding end 234 of the male component 210, and the second bore portion may have a diameter sized to accommodate the projections 240 after the projections 240 are moved to the locking configuration. In the locking configuration, the projections 240 may extend radially beyond the diameter of the first bore portion 262.

In some embodiments, the projections 240 are movable, in response to a change in temperature, between the insertion configuration and the locking configuration. For example, the projection 240 may be made of a memory material that is configured to move to an insertion configuration in response to an insertion temperature within an insertion temperature range being applied. In some examples, a shape memory alloy such as Nitinol may be used to form the projections 240.

In one specific example, the insertion temperature range is greater than a locking temperature range. For example, an insertion temperature may be greater than 140 degrees Fahrenheit while a locking temperature range is less than 120 degrees Fahrenheit. In another specific example, the insertion temperature range is less than the locking temperature range. For example, an insertion temperature range may be less than 32 degrees Fahrenheit, while a locking temperature range is greater than 50 degrees Fahrenheit. Of course, other temperature ranges may be used to move the projection to an insertion configuration while outside of the body of a patient while the locking temperature range may be close to a normal body temperature of 98.6 degrees Fahrenheit (e.g., between 80 degrees Fahrenheit and 120 degrees Fahrenheit).

In one exemplary embodiment, the male component 210 includes a bone engagement end 235 that is implantable into the bore 130 of the first bone segment 110. In certain embodiments, the bone engagement end 235 includes one or more bone engagement features that will be further described in FIG. 3.

Further, in an exemplary embodiment, the protruding end 234 of the male component 210 defines a protrusion axis 252. In FIG. 2, the protrusion axis is 252 coaxial with the bore axis of the receiving end bore 238 of the female component 220. In one example, the protrusion 245 extends along the protrusion axis 252 and includes the projections 240, which extend axially from the distal end of the protrusion 245 and bend toward a bore wall within the receiving end bore 238 of the female component 220.

In certain exemplary embodiments, the angle at which the projections 240 are bent may be based on a current temperature of the projections 240. As previously described, in an insertion temperature range, the projections 240 may be bent so that the projections 240 do not extend radially beyond a diameter of a first bore portion 262. In another example, in response to heating or cooling of the projection 240 from the insertion temperature range to a locking temperature range, the projections 240 bend to extend further radially to exceed the diameter of the first bore portion 262. Thus, at the locking temperature range and after being inserted into the receiving end 224 of the female component 220, the projections 240 may extend radially to exceed the diameter of the first bore portion 262 so that extraction of the protruding end 234 of the male component 210 from the receiving end bore 238 of the female component 220 is restricted and/or precluded. The second bore portion 264 may define an internal cavity 236 having sufficient space to allow the projections 240 to flex between the insertion configuration and the locking configuration. As mentioned previously, this change in configurations may be induced by a change in temperature of the projections 240, between the insertion temperature range and the locking temperature range. Optionally, in the locking configuration, the outer end of each of the projections 240 presses against a shoulder 652 between the first bore portion 262 and the second bore portion 264 to urge the protrusion 245 to move deeper into the receiving end bore 238, thereby tightening the engagement between the male component 210 and the female component 220.

In one exemplary embodiment, each of the projections 240 substantially consists of Nickel and Titanium at approximately equal portions. In one example, each of the projections 240 comprises 50% Nickel by atomic percentage and/or 55% Nickel by weight. Of course, one skilled in the art may recognize other types of materials exhibit a memory effect in certain temperature ranges and this disclosure includes all such materials.

Figure 3:
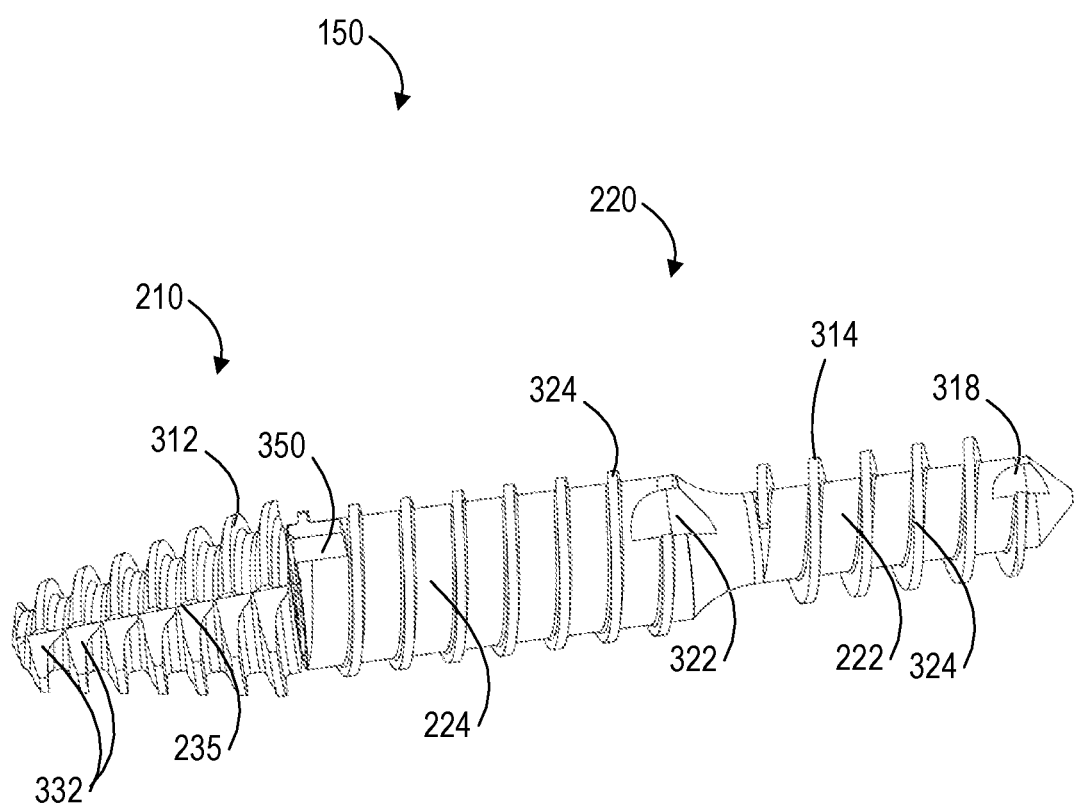
FIG. 3 is a perspective view depicting the bone segment attachment system with the female component and male component engaged with each other.

FIG. 3 is a perspective view depicting the bone segment attachment system 150 with the female component 220 and male component 210 engaged with each other. In this exemplary embodiment, FIG. 3 more clearly shows various bone engagement features of the male component 210 and the female component 220.

As one skilled in the art may appreciate, bone engagement features may include helical threads, barbs, or any other feature that allows a bone engagement end such as the bone engagement end 235 and the bone engagement end 222 to be inserted into the bores 130 of the first bone segment 110 and the bore 140 of the second bone segment 120 and helps retain the bone engagement end 235, 222 within the bore 130, 140. In one specific embodiment, the bone engagement features of the male component 210 are helical threads 312 on the bone engagement end 235 of the male component 210, and the bone engagement features of the female component 220 are helical threads 314 on the bone engagement end 222 of the female component 220.

When the bone engagement end 222 of the female component 220 is inserted into the bore 140 of the second bone segment 120 and the female component 220 is rotated, bone fragments and/or fluids may be displaced from the bore 140, and the female component 220 may be pulled into the bore 140 of the second bone segment 120. Similarly, when the bone engagement end 235 of the male component 210 is inserted into the bore 130 of the first bone segment 110 and the male component 210 is rotated, bone fragments and/or fluids may be displaced from the bore 130, and the male component 210 may be pulled into the bore 130 of the first bone segment 110.

Further, the bone engagement end 222 of the female component 220 shows an exemplary embodiment of a pair of cutting features in the form of reliefs 318, 322 that may facilitate insertion of the bone engagement end 222 into the bore 140 of the second bone segment 120. For example, during insertion of the bone engagement end 222 into the bore 140, the reliefs 318 may help dislodged bone matter and/or fluids to move from in front of the tip of the advancing bone engagement end 222 to the spaces between the helical threads 314 of the bone engagement end 222, and thence, out of the bore 140. The reliefs 318 are shown placed at different locations along the length of the bone engagement end 222; however, these locations are merely exemplary, as one skilled in the art may place the reliefs 318, 322 different locations.

Similar cutting features may be used on the bone engagement end 235 of the male component 210. Specifically, the bone engagement end 235 may have cutting features in the form of breaks 332 in the helical threads 312 of the bone engagement end 235. The breaks 332 may also permit dislodged bone and/or fluids to move out of the bore 130 during insertion of the bone engagement end 235 into the bore 130.

As mentioned previously, the receiving end bore 238 may be accessible via the opening 270 in the receiving end 224 of the female component 220. The opening 270 may have a break 350, which may be used, for example, to apply torque to the female component 220 during insertion. For example, an insertion instrument (not shown) may have a keyhole-shaped feature on its distal end that is received within the opening 270 and the break 350, permitting the keyhole-shaped feature to impart torque to screw the female component 220 into the bore 140 of the second bone segment 120.

Figure 4:
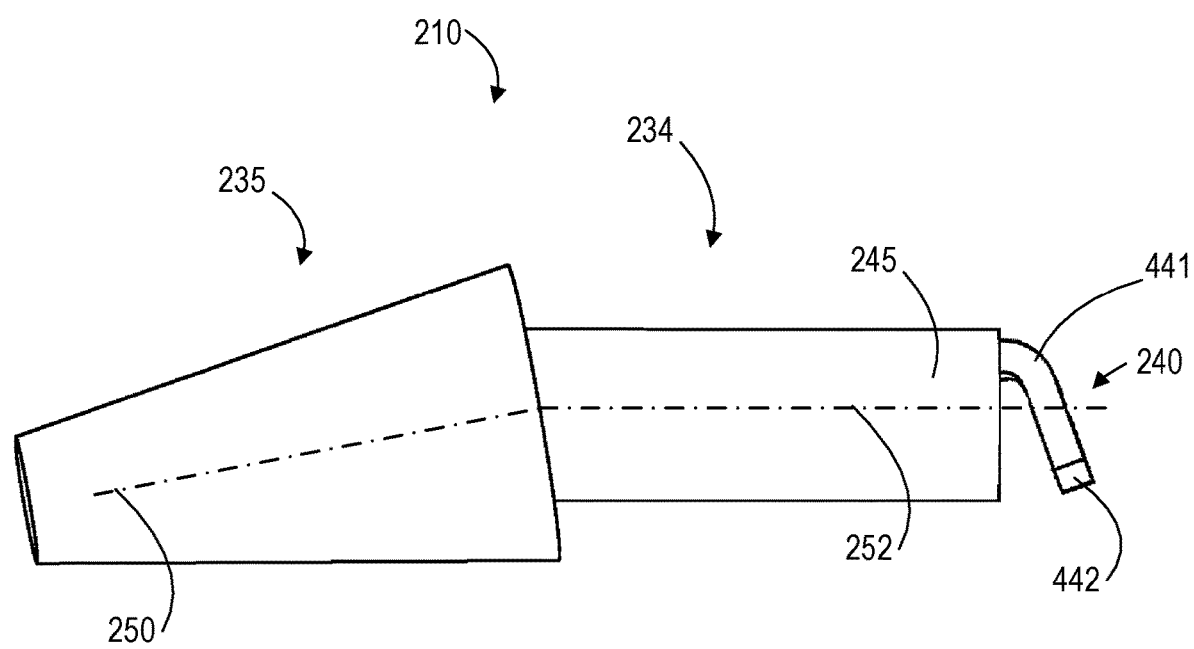
FIG. 4 is a side elevation, section view of the male component in the insertion configuration.

FIG. 4 is a side elevation, section view of the male component 210 in the insertion configuration. As mentioned previously, the protrusion 245 of the protruding end 234 may extend along a protrusion axis 252. Notably, the bone engagement end 235 may extend along a bone engagement axis 250 that is different from the protrusion axis 252.

In one exemplary embodiment, the protrusion axis 252 of the protrusion 245 is not parallel to the bone engagement axis 250 of the bone engagement end 235. In this way, the bone segment attachment system 150 may orient the first bone segment 110 and the second bone segment 120 at different orientations from each other. For example, the bone engagement end 235 may be engaged with the first bone segment 110 and rotated to a desired orientation such that the first bone segment 110 is angled a predetermined number of degrees from the second bone segment 120, allowing the first bone segment 110 to be positioned at a relatively natural orientation relative to the second bone segment 120. The angular difference between the protrusion axis 252 and the bone engagement axis 250 may be selected to provide this desired angular offset between the first bone segment 110 and the second bone segment 120. This angular offset may be within the range of 0° to 45°. Further, the angular offset may be within the range of 2.5° to 35°. Yet further, the angular offset may be within the range of 5° to 25°. Still further, the angular offset may be within the range of 7.5° to 15°. Yet further, the angular offset may be about 10°.

In one example embodiment, the projections 240 are, prior to insertion of the protrusion 245 into the receiving end bore 238, at an insertion temperature within the insertion temperature range. The insertion temperature may be at or near room temperature; thus, the insertion configuration may be the default state for the projections 240. In the alternative, the projections 240 may be heated or cooled to an insertion temperature greater or less than room temperature. In response to the heating or cooling, the projections 240 may move to the insertion configuration. As mentioned previously, in the insertion configuration, the projections 240 may not extend passed the diameter of the first bore portion 262, thus allowing the protruding end 234 of the male component 210 to be inserted into the receiving end 224 of the female component 220 without obstruction.

In the insertion configuration, ends 442 of the projections 240 may slide along the interior surface of the first bore portion 262 during insertion. In the alternative, the ends 442 of the projections 240 may be retracted sufficiently away from the interior surface of the first bore portion 262 to avoid contact with the first bore portion 262 during insertion.

According to certain exemplary embodiments, each of the projections 240 includes a sensitive portion 441 that undergoes a more dramatic change in shape than other portions of the projections 240, in response to a change in temperature. This sensitive portion 441 may flex according to the temperature to cause the projection 240 to either bend away from the protrusion 245 to bring the ends 442 of the projections 240 inside the diameter of the first bore portion 262, or to bend toward the protrusion 245 to extend the ends 442 of the projections 240 beyond the diameter of the first bore portion 262.

In FIG. 4, the projections 240 are in the insertion configuration because they are bent at obtuse angles in which they do not extend outward, radially, beyond the radius of the first bore portion 262. Thus, as configured in FIG. 4, the projections 240 do not mechanically interfere with insertion of the protruding end 234 into the receiving end bore 238. As mentioned previously, the tips of the projections 240 may be angled to such that, in the insertion configuration of FIG. 4, they are generally parallel to the interior wall of the receiving end bore 238.

Figure 5:
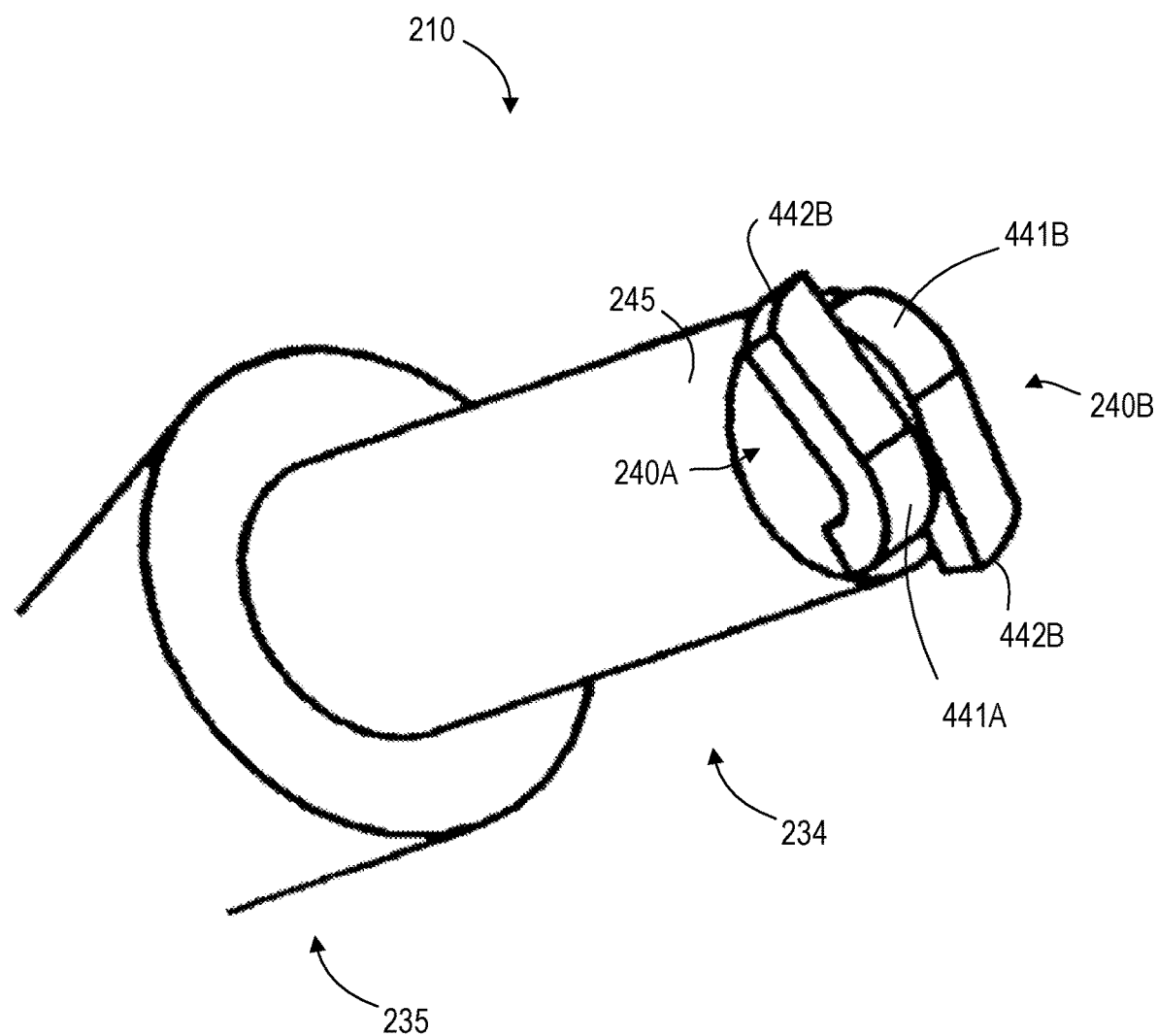
FIG. 5 is a perspective view of the male component of the bone segment attachment system, in the locking configuration, as in FIG. 2.

FIG. 5 is a perspective view of the male component 210 of the bone segment attachment system 150, in the locking configuration, as in FIG. 2. In this example embodiment, there are two projections 240A, 240B. In this example, the two projections 240 diametrically opposed to each other and positioned and oriented with radial symmetry about the protrusion axis 252. The respective projections 240A 240B include respective sensitive portions 441A, 441B. In this example embodiment, the projections 240A, 240B may be similarly configured so that they change into insertion configurations and locking configuration at substantially the same temperatures, but, of course, this is not necessarily the case.

In other exemplary embodiments (not shown), there are three or more projections 240 that, in the locking configuration, are each configured to extend beyond the diameter of a portion of the receiving end bore 238 of the receiving end 224 of the female component 220 as previously described. Where there are multiple projections, they may or may not have identical shapes, and may or may not be radially-symmetrically disposed about the protrusion axis 252. Further, in some exemplary embodiments (not shown), only one projection 240 may be present.

Figure 6:
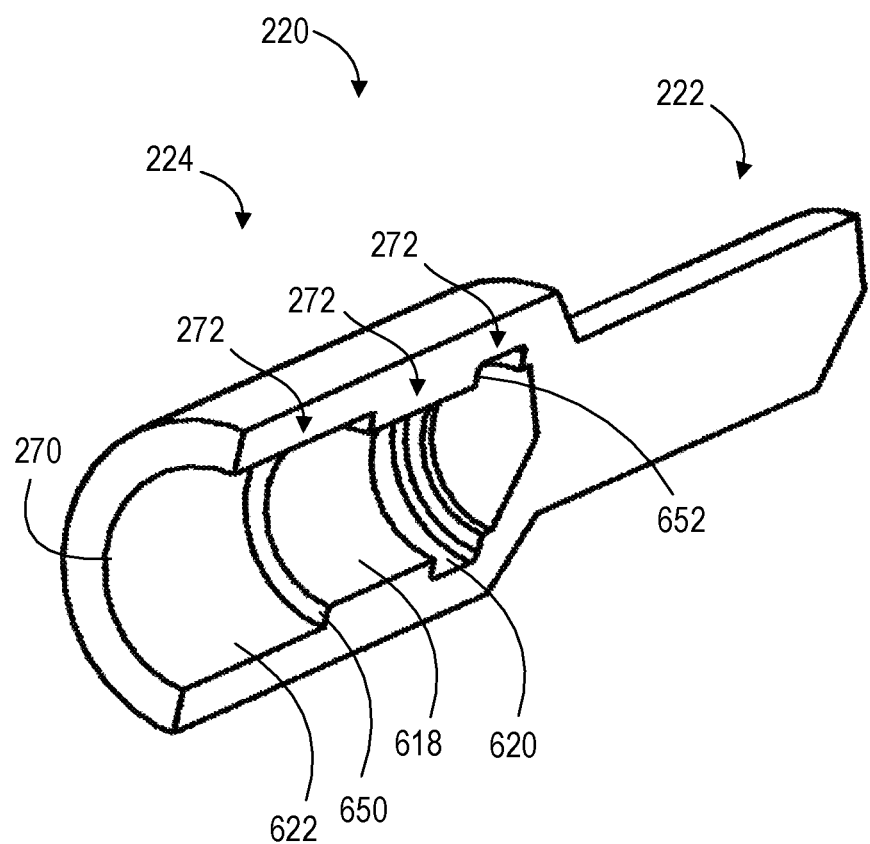
FIG. 6 is a perspective, section view of the female component of the bone segment attachment system of FIG. 1.

FIG. 6 is a perspective, section view of the female component 220 of the bone segment attachment system 150 of FIG. 1. The view of FIG. 6 depicts the geometry of the receiving end bore 238, including one or more bore walls (e.g., the first bore portion 262, the second bore portion 264, and the third bore portion 272). In this exemplary embodiment, the receiving end bore 238 includes a first bore wall 618 of the first bore portion 262, a second bore wall 620 of the second bore portion 264, and a third bore wall 622 of the third bore portion 272.

The third bore portion 272 may have a diameter that is larger than that of the protruding end 234 of the male component 210. The opening 270 may share the diameter of the third bore portion 272. This clearance may facilitate insertion of the protruding end 234 of the male component 210 into the receiving end bore 238 through the opening 270.

The first bore portion 262 may have a diameter that is substantially similar to, or slightly larger than, the diameter of the protruding end 234 of the male component 210. This limited clearance may keep the protruding end 234 of the male component 210 parallel to the receiving end 224 of the female component 220, thereby ensuring that the male component 210 and the female component 220 obtain the proper relative orientation. This may, in turn, cause the first bone segment 110 to have the desired natural orientation relative to the second bone segment 120. The limited clearance between the first bore portion 262 and the protruding end 234 may also help lock the protruding end 234 in place within the receiving end bore 238 by limiting the amount of radial expansion required for the projections 240 to interfere with passage of the protruding end 234 back through the first bore portion 262.

In some alternative examples, the first bore portion 262 and the protruding end 234 may be sized such that there is very little clearance, or even such that there is slight interference between the first bore portion 262 and the protruding end 234. Such interference may be, for example, about ten micrometers, and may cause the protruding end 234 to fit tightly in the receiving end bore 238, thereby preventing undesired relative motion (in particular, rotation) between the male component 210 and the female component 220 that may not otherwise be locked out by the projections 240 in the locking configuration.

In this particular embodiment, the first bore portion 262 has a diameter larger than the insertion diameter, centered at the protrusion axis 252, which circumscribes the projections 240 in the insertion configuration. The diameter of the first bore portion 262 may be smaller than the locking diameter, centered at the protrusion axis 252, which circumscribes the projections 240 in the locking configuration. Thus, the protruding end 234 may not be insertable into the receiving end 224 unless the projections 240 are in the insertion configuration due to interference of the projections 240 with the first bore wall 618 of the first bore portion 262.

Further, in this embodiment, the second bore portion 264 has a diameter that is larger than the diameter of the first bore portion 262. Additionally, the diameter of the second bore portion 264 may be larger than the insertion diameter and larger than the locking diameter referenced above, thus allowing the projections 240 to move to the locking configuration within the second bore portion 264 after the projections 240 have been inserted beyond the end of the first bore portion 262.

In another example embodiment (not shown), the first bore portion 262 and the second bore portion 264 may have substantially the same diameter, which may be smaller than the locking diameter of the projections 240 referenced above, but larger than the insertion diameter of the projections 240 referenced above. In this embodiment, the protruding end 234 may also be inserted into the receiving end bore 238 until the projections 240 are past the end of the first bore portion 262, and within the second bore portion 264.

Returning to the embodiment depicted in FIG. 6, in which the first bore portion 262 has a smaller diameter than that of the third bore portion 272, a shoulder 650 may exist between the first bore portion 262 and the third bore portion 272. The shoulder 650 may have an annular shape residing in a plane perpendicular to the axis of the receiving end bore 238. In the alternative, the shoulder 650 may be frustoconical in shape, with a taper that facilitates insertion of the protruding end 234 by guiding the protruding end 234 to the center of the first bore portion 262.

Further, as mentioned previously, the diameter of the second bore portion 264 may be larger than that of the first bore portion 262. Thus, a shoulder 652 may exist between the first bore portion 262 and the second bore portion 264. The shoulder 652 may have an annular shape residing in a plane perpendicular to the axis of the receiving end bore 238. In the alternative, the shoulder 652 may have a frustoconical shape tapered toward the bone engagement end 222 of the female component 220, providing a lip (not shown) that protrudes toward the bone engagement end 222. With such a taper, a projection that is in the locking configuration may hook on the lip of the shoulder 652; this hooking motion may increase resistance to unintended withdrawal of the protruding end 234 of the male component 210 from the receiving end bore 238 of the female component 220.

The female component 220 as shown in FIG. 6 has both a smaller diameter at the bone engagement end 222 and larger diameter at the receiving end 224. The smaller diameter of the bone engagement end 222 may enter the bore 140 of the second bone segment 120 first and may serve to guide the larger diameter of the receiving end 224 into the bore 140. The smaller diameter of the bone engagement end 222 may reduce the possibility of splitting the second bone segment 120 as the bone engagement end 222 is inserted into the bore 140. The helical threads 314 secure the bone engagement end 222 of the female component 220 in place within the bore 140.

Notably, the female component 220 may be designed to reside nearly or completely within the bore 140 of the second bone segment 120 so that the surrounding surface of the second bone segment 120 can be drawn into contact, or into near-contact, with the adjacent surface of the first bone segment 110 to promote fusion between the first bone segment 110 and the second bone segment 120. Thus, after insertion of the bone engagement end 222 into the second bone segment 120, the receiving end 224 may also be inserted into the bore 140 of the second bone segment 120.

The receiving end 224 may also have bone engagement features that help to retain the receiving end 224 within the second bone segment 120. Like the bone engagement features of the bone engagement end 222, which may be helical threads 312 as described above, the bone engagement features of the receiving end 224 may be ridges, barbs, deployable extensions, expandable elements, and/or any other bone engagement features known in the art. In FIG. 3, the bone engagement features of the receiving end 224 are helical threads 324. These helical threads 324 may protrude radially from the minor diameter between them only modestly, such that the major diameter of the helical threads 324 of the receiving end 224 is the same as, or only slightly greater, than that of the helical threads 314 of the bone engagement end 222. As the receiving end 224 enters the second bone segment 120, it may compact the surrounding bone, providing for secure fixation of the receiving end 224 within the bore 140 of the second bone segment 120 without the need for the helical threads 324 to be larger.

Figure 7:
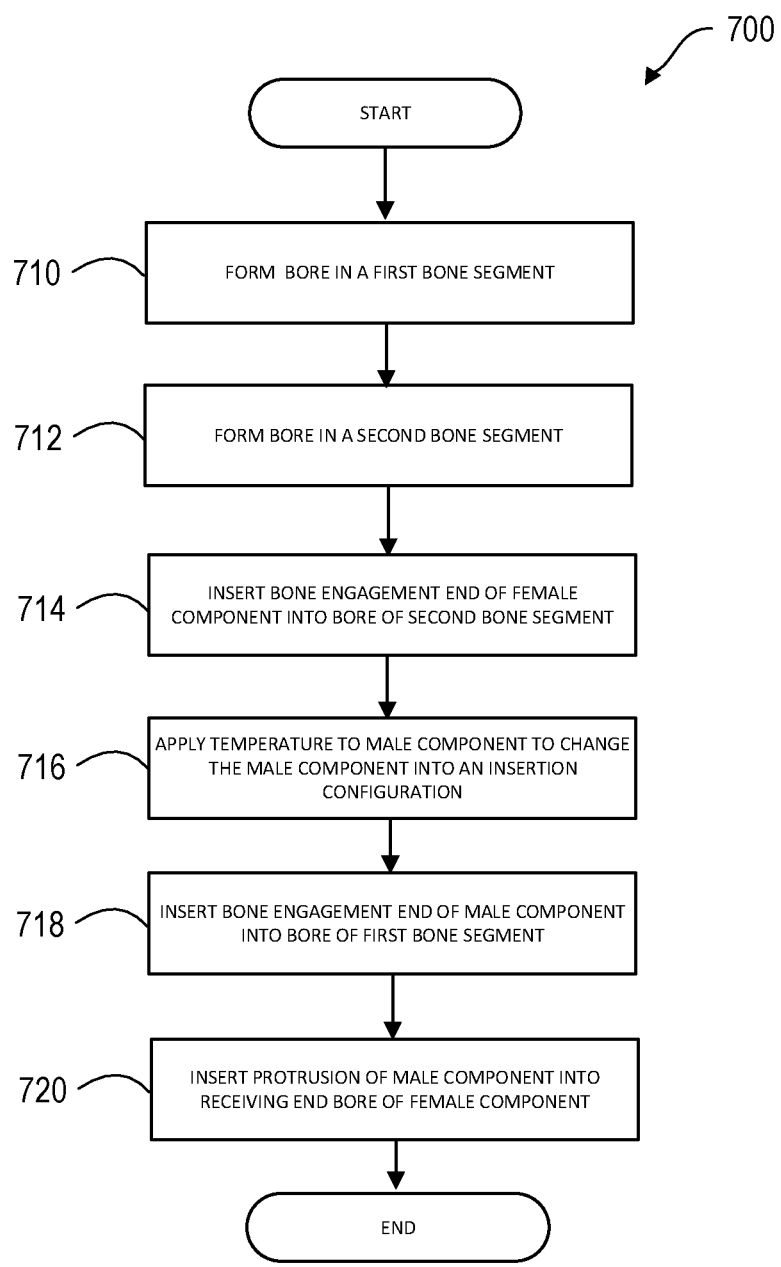
FIG. 7 is a flow diagram depicting a method of implanting the bone segment attachment system of FIGS. 1-6, according to one exemplary embodiment.

FIG. 7 is a flow diagram depicting a method 700 of implanting the bone segment attachment system 150 of FIGS. 1-6, according to one exemplary embodiment. The method 700 begins and at step 710, in which the bore 130 is formed in the first bone segment 110. In one example, a user may drill, ream, or otherwise form the bore 130 through the use of an instrument. In alternative embodiments, the bone engagement end 235 of the male component 210 may be designed to form the bore 130 during insertion, such that the bore 130 need not be formed prior to insertion of the bone engagement end 235 into the first bone segment 110. Rather, the process of inserting the bone engagement end 235 into the first bone segment 110 may form the bore 130.

In a step 712, the bore 140 is formed in the second bone segment 120. As in the step 710, the bore 140 may be formed through the use of one or more tools known in the art, and/or through the use of bore-forming functionality in the bone engagement end 222 of the female component 220.

In a step 714, the bone engagement end 222 of the female component 220 is inserted into the bore 140 of the second bone segment 120. In certain examples, the female component 220 is screwed or pressed into the bore 140 in the second bone segment 120.

In a step 716, heating or cooling is applied the projections 240 until the projections 240 change to the insertion configuration. As one skilled in the art may appreciate, the insertion temperature may be reached in many different ways. In some examples, where the insertion temperature is higher than a locking temperature, heat is applied using a torch, an oven, a heated liquid in which the projections 240 are dipped, electromagnetic waves, contacting the projection with a heated material, or other heat transfer techniques. The heat may be applied to the whole of the male component 210 or simply to the projections 240.

In another example, the insertion temperature range is lower than the locking temperature range. In this example, a temperature of the male component 210, or the projection 240 of the male component 210, is lowered to the insertion temperature by inserting the projections 240 into a refrigerated space, dipping the projections 240 into a colder material (e.g., liquid nitrogen), contacting the projections 240 with a cooled material, or via any other known cooling method, as one skilled in the art may appreciate. Cooling may be applied to the whole of the male component 210 or simply to the projections 240.

In yet another example, the insertion temperature is near room temperature. In such a case, the step 716 may be omitted, as the male component 210 may be stored at the insertion temperature, and may thus be stored with the projections 240 in the insertion configuration.

In a step 718, the bone engagement end 235 of the male component 210 is inserted into the bore 130 of the first bone segment 110. In certain examples, the male component 210 is screwed or pressed into the bore 130 in the first bone segment 110.

In a step 720, the protrusion 245 of the male component 210 is inserted into the receiving end bore 238 of the female component 220. If desired, the first bone segment 110 may be rotated to a desired orientation relative to the second bone segment 120 prior to insertion of the protrusion 245 into the receiving end bore 238. Alternatively, the protrusion 245 may be inserted into the receiving end bore 238 and then the first bone segment 110 may be oriented as desired relative to the second bone segment 120. Where there is little clearance or some interference between the protrusion 245 and the first bore portion 262, the protrusion 245 may be pressed, either by hand or via an instrument, into the receiving end bore 238 until the projections 240 have entered the second bore portion 264.

In one exemplary embodiment, the male component 210, with the projections 240 at the insertion temperature, is inserted into the receiving end bore 238 to position the projections 240 in the second bore portion 264 before the male component 210 changes to the locking configuration. Then, as the bone segment attachment system 150 acclimates to the temperature of the body, causing the male component 210 to move to the locking configuration in which the projections 240 impede withdrawal of the protrusion 245 from the receiving end bore 238.

The surgical wound site may then be closed. According to an optional step, a brace, cast, or other device (not shown) may be attached to the patient's toe, of which the first bone segment 110 and the second bone segment 120 are part, to keep the first bone segment 110 in the desired position and orientation relative to the second bone segment 120 until bone in-growth can occur between the first bone segment 110 and the second bone segment 120.

Figure 8:
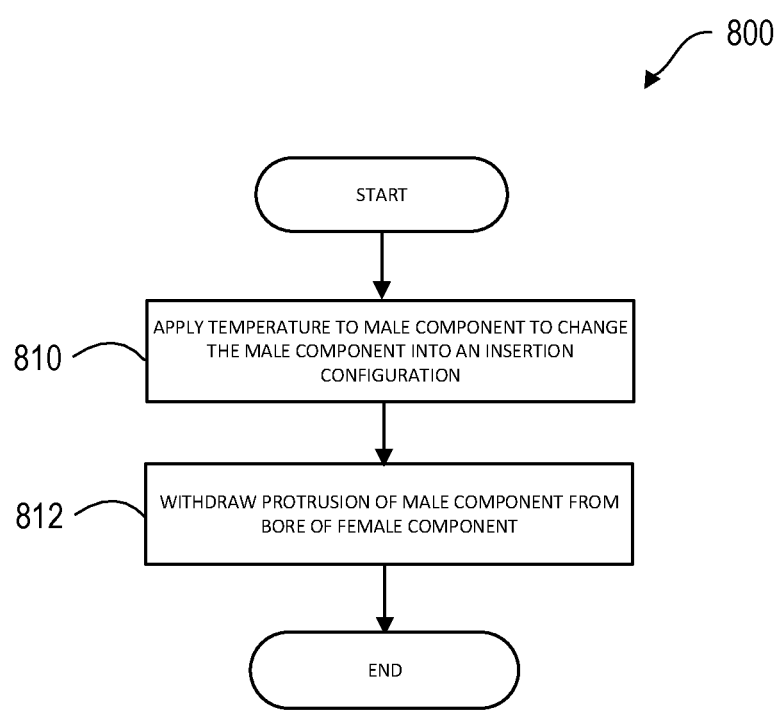
FIG. 8 is a flow diagram depicting a method of decoupling the first bone segment and the second bone segment after implantation of the bone segment attachment system, as in the method of FIG. 7, according to one exemplary embodiment.

FIG. 8 is a flow diagram depicting a method 800 of decoupling the first bone segment 110 and the second bone segment 120 after implantation of the bone segment attachment system 150, as in the method 700 of FIG. 7, according to one exemplary embodiment. The method 800 begins and at step 810, in which heating or cooling is applied to the male component 210 until the projections 240 return to the insertion temperature range. In one example, the male component is heated. In another example, the male component is cooled. If this is a revision procedure, some bone growth may have occurred between the first bone segment 110 and the second bone segment 120; accordingly, the step 810 may include, if needed, breaking the second bone segment 120 apart from the first bone segment 110.

In a step 812, the protrusion 245 of the male component 210 may be withdrawn from the receiving end bore 238 of the female component 220. Once the protrusion 245 is out of the receiving end bore 238, the joint and/or the bone segment attachment system 150 may be revised as needed.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system for attaching a first bone segment and a second bone segment together, the system comprising:
a first component comprising:
a first component bone engagement end implantable into a first bore formed in the first bone segment; and
a first component attachment end; and
a second component comprising:
a second component bone engagement end implantable into a second bore formed in the second bone segment; and
a second component attachment end comprising a first projection that is movable, in response to a temperature change of the first projection, between:
an insertion configuration in which, with the second component attachment end assembled together with the first component attachment end, the first projection is positioned such that the first projection does not interfere with withdrawal of the second component attachment end from the first component attachment end; and
a locking configuration in which, with the second component attachment end assembled together with the first component attachment end, the first projection is positioned to interfere with withdrawal of the second component attachment end from the first component attachment end.

2. The system of claim 1, wherein:
the first bone segment comprises one of a proximal phalanx and a middle phalanx; and
the second bone segment comprises the other of the proximal phalanx and the middle phalanx.

3. The system of claim 1, wherein:
the first component attachment end comprises an attachment end bore; and
the second component attachment end comprises a protrusion insertable into the attachment end bore, the protrusion comprising the first projection.

4. The system of claim 3, wherein:
the attachment end bore is accessible through an opening in the first component attachment end;
the attachment end bore comprises:
a first bore portion having a first bore wall, with a first diameter;
a second bore portion having a second bore wall positioned such that the first bore wall is between the second bore wall and the opening, the second bore wall having a second diameter larger than the first diameter; and
a shoulder extending generally radially between the first bore wall and the second bore wall;
with the second component attachment end assembled together with the first component attachment end, the first projection is within the second bore portion;
in the insertion configuration, the first projection does not extend radially beyond the first diameter; and
in the locking configuration, the first projection extends radially beyond the first diameter such that the first projection is positioned to interfere with withdrawal of the protrusion from the attachment end bore.

5. The system of claim 4, wherein:
the first projection comprises a rod that, with the first projection positioned within the second bore portion of the attachment end bore, is bent toward the second bore wall;

in the insertion configuration, the rod is bent at an obtuse angle; and in the locking configuration, the rod is bent at an acute angle.

6. The system of claim 4, wherein:

the protrusion defines a protrusion axis;

the protrusion further comprises a second projection positioned on an opposite side of the protrusion axis from the first projection; and the second projection is also movable, in response to the temperature change, between the insertion configuration and the locking configuration.

7. A system for attaching a proximal phalanx to a middle phalanx, the system comprising:

a female component comprising:

a female component bone engagement end implantable into a first bore formed in one of the proximal phalanx and the middle phalanx, the female component bone engagement end comprising one or more female component bone engagement features configured to engage the first bore to retain the female component bone engagement end within the first bore; and a receiving end comprising a receiving end bore defining a bore axis, wherein the receiving end bore is accessible through an opening, the receiving end bore comprising:

a first bore portion having a first bore wall, with a first diameter; and a second bore portion having a second bore wall positioned such that the first bore wall is between the second bore wall and the opening, the second bore wall having a second diameter larger than the first diameter;

a male component comprising:

a male component bone engagement end implantable into a second bore formed in the other of the proximal phalanx and the middle phalanx, the male component bone engagement end comprising one or more male component bone engagement features configured to engage the second bore to retain the male component bone engagement end within the second bore; and a protruding end comprising a protrusion defining a protrusion axis, the protrusion comprising a first projection that is movable, in response to a temperature change of the first projection, between:

an insertion configuration in which the first projection does not extend radially beyond the first diameter; and a locking configuration in which the first projection extends radially beyond the first diameter such that the first projection is positioned to interfere with withdrawal of the protrusion from the receiving end bore.

8. The system of claim 7 wherein:

the receiving end bore further comprises a shoulder extending generally radially between the first bore wall and the second bore wall; and the first projection, in the locking configuration, presses against the shoulder.

9. The system of claim 8, wherein the first projection comprises a rod that, with the first projection positioned within the second bore portion of the receiving end bore, is bent toward the second bore wall.

10. The system of claim 9, wherein;

in the insertion configuration, the rod is bent at an obtuse angle; and in the locking configuration, the rod is bent at an acute angle.

11. The system of claim 7, wherein:

the protrusion further comprises a second projection positioned on an opposite side of the protrusion axis from the first projection; and the second projection is also movable, in response to the temperature change, between the insertion configuration and the locking configuration.

12. The system of claim 7, wherein the first projection is formed at least partially of Nitinol.

13. The system of claim 7, wherein the temperature change comprises cooling the first projection to cause the first projection to move from the insertion configuration to the locking configuration.

14. The system of claim 7, wherein the temperature change comprises heating the first projection to cause the first projection to move from the insertion configuration to the locking configuration.

15. The system of claim 7, wherein the male component bone engagement end defines a bone engagement axis nonparallel to the protrusion axis.

* * * * *